United States Patent [19]

Stoutamire

[11] 4,176,195

[45] Nov. 27, 1979

[54] PESTICIDAL α-CYANOBENZYL ESTER ENANTIOMER PAIR

[75] Inventor: Donald W. Stoutamire, Modesto, Calif.

[73] Assignee: Sumitomo Chemical Company, Limited, Osaka, Japan

[21] Appl. No.: 926,366

[22] Filed: Jul. 20, 1978

[51] Int. Cl.$^2$ .......................... A01N 9/06; A01N 9/20; C07C 121/50; C07C 121/60
[52] U.S. Cl. ................................. 424/304; 260/465 D
[58] Field of Search .......................... 424/304; 260/465

[56] References Cited

U.S. PATENT DOCUMENTS

| | | | |
|---|---|---|---|
| 3,996,244 | 12/1976 | Fujimoto et al. | 424/282 |
| 4,058,622 | 11/1977 | Fujimoto et al. | 424/304 |

FOREIGN PATENT DOCUMENTS

| | | |
|---|---|---|
| 801946 | 7/1973 | Belgium . |
| 75/25544 | 8/1975 | Japan . |
| 75/106935 | 10/1975 | Japan . |

OTHER PUBLICATIONS

Chem. Abst. 84, 30685(d), (1976),—Gerasimova et al.
Chem. Abst. 85, 187,457(2), (1976),—Miura et al.
Pest. Science 1,273–1,277, (1976).

*Primary Examiner*—Douglas W. Robinson

[57] ABSTRACT

An enantiomer pair consisting of S-α-cyano-3-phenoxybenzyl S-α-isopropyl-p-chlorophenylacetate and R-α-cyano-3-phenoxybenzyl R-α-isopropyl-p-chlorophenylacetate, said pair substantially free of other stereoisomers is a highly active pesticide.

4 Claims, No Drawings

PESTICIDAL α-CYANOBENZYL ESTER ENANTIOMER PAIR

BACKGROUND OF THE INVENTION

1. Field of the Invention

The present invention is directed to a new composition, an enantiomer pair of an α-cyanobenzyl ester having useful pesticidal activity.

2. Description of the Prior Art

It is known from *Pesticide Science, Vol 7*, pages 273–77 (1976) and earlier work that the optical configuration of individual isomers of cyclopropanecarboxylate "pyrethroids" affects their insecticidal toxicity, and that in racemic mixtures of at least one pyrethroid ester derived from chrysanthemic acid there is mutual antagonism between pairs of isomers so that considerable masking of activity occurs.

Certain esters of substituted-phenylacetic acids are described in Belgian patent publication No. 801,946 as having pyrethroid-like properties, including pesticidal activity and low toxicity to mammals. It is further known how to prepare or to recover the S- optical form of such phenylacetic acids, e.g., Japanese patent publications Nos. 75/25,544 and 75/106,935, and that the pyrethroid esters of such S-acids were approximately twice as insecticidal as the corresponding racemate derived from both the S- and R- forms of such acids. The α-cyano-3-phenoxybenzyl ester diastereoisomer pair derived from the S-form of α-isopropyl-p-chlorophenylacetic acid can be separated into the single diastereoisomers and when tested for pesticidal activity, the stereoisomer (−)-S-α-cyano-3-phenoxybenzyl S-α-isopropyl-p-chlorophenylacetate was found to be up to several times more active than the double racemate derived from the R,S-alcohol and the R,S-acid and about twice as active as the diastereoisomer pair derived from the S-acid.

However, the procedures to prepare or recover the S- optical form of the phenylacetic acids is costly, time-consuming and requires considerable amounts of additional reagents, such as α-phenylethylamine, or highly caustic materials such as alkali or alkaline earth hydroxides or carbonates which are employed at temperatures in excess of 110° C. One such process involves the resolution of a mixture of R,S-phenyl-acetic acid stereoisomers by stirring the stereoisomer mixture in warm aqueous ethanol with an equal number of moles of (−)-α-phenylethylamine to form a salt, cooling the mixture to form crystals of the salt of the S-acid, which is less soluble than the salt of the R-acid, separating the crystallized salt of the S-acid by filtration, washing the crystals with aqueous ethanol, and recovering the S-acid (a) using aqueous caustic and toluene to separate the S-acid, which dissolves in the aqueous phase, from the amine, which extracts into the toluene phase or (b) by addition of the salt to aqueous acid to precipitate the S-acid. The R-acid present in the original reaction mixture can be similarly recovered from the salt using aqueous ethanol and then aqueous caustic and toluene treatment or from the salt by treatment with acid. The R-acid is racemized and recycled for admixture with fresh feed mixture of R,S-phenylacetic acid stereoisomers.

By contrast, a highly active pesticidal stereoisomer mixture of a phenylacetate has been found which is much easier and economical to prepare than either the above diastereoisomer pair derived from the S—form of the acid or any single diastereoisomer, while providing improved pesticidal activity as compared to the racemate of the prior art.

SUMMARY OF THE INVENTION

The present invention is directed to an enantiomer pair consisting of S-α-cyano-3-phenoxybenzyl S-α-isopropyl-p-chlorophenylacetate and R-α-cyano-3-phenoxybenzyl R-α-isopropyl-p-chlorophenylacetate, substantially free of other stereoisomers, which is a highly active pesticide.

This pair is obtained by cooling a solution of a racemic mixture of R,S-α-cyano-3-phenoxybenzyl R,S-α-isopropyl-p-chlorophenylacetate in a suitable solvent to effect crystallization. The racemic mixture is known from Belgian patent publication No. 801,946.

Such crystallization is conducted in a solvent from which the desired enantiomer pair preferentially crystallizes. Suitable solvents are hydroxylic solvents, e.g., lower alkanols containing from 1 to 4 carbon atoms such as isopropanol, butanol, ethanol, and methanol, and preferably containing from 1 to 2 carbon atoms, especially methanol. Lower alkanes containing 1 to 8 carbon atoms may also be used as solvents. For best results, the differential solubilities of the two enantiomer pairs in the solvent should be high.

The crystallization is conducted by preparing a solution of the racemate in a suitable solvent as defined above. The crystallization proceeds normally over a period of time, usually several days. The process can be conducted at any temperature at which crystals of the desired enantiomer pair form, suitably −50° to 20° C. and preferably −15° to 5° C.

Separation and recovery of the solid (crystalline) product from the crystallization is achieved by methods such as filtration, centrifugation or decantation of the mother liquor.

The enantiomer pair of the invention is also conveniently prepared from the double racemate by chromatographic procedures. The racemate is passed through a chromatographic column containing a suitable packing material, for example, silica gel, using an eluant liquid, for example, 1% diethyl ether in hexane. The desired enantiomer pair is recovered as the later emerging of the two enantiomer pairs recovered from the process.

The enantiomer pair of the invention is a highly active pesticide. When tested against various pests at equal rates per volume, the enantiomer pair of the invention is several times more active than the earlier emerging enantiomer pair and, moreover, even about twice as active as the racemic mixture from which it is prepared. The pesticidal activity is even higher when the crystalline form of the enantiomer pair of the invention is utilized.

The enantiomer pair is an oily liquid in its low purity form, e.g., about 80% pure, but in higher purity, e.g., about 95% pure or more, the enantiomer pair forms a crystalline solid having a melting point of 45°–55° C.

The superior activity of the enantiomer pair of the invention is usefully employed when it is present in amounts greater than that present in the usual racemate produced when racemic R,S- form of α-isopropyl-p-chlorophenylacetic acid is esterified with the racemic R,S-α-cyano-3-phenoxybenzyl alcohol (or derivative thereof, such as halides). Therefore, use of the enantiomer pair of the invention in a form substantially free of other stereoisomers is preferred, e.g., in an enantiomer pair purity of greater than about 80%, more preferably in an enantiomer pair purity greater than about 90% or even greater than about 95% of the enantiomer pair.

The enantiomer pair of the invention is employed to combat, control or eradicate pests including insects and acarines using conventional methods and formulations. The enantiomer pair or formulation thereof is applied to the pests, their habitat or the like. The pesticidally effective amount of the enantiomer pair used will vary with the particular pest to be controlled and the method or formulation used. Thus, the invention is also directed to a method employing a pesticidally effective amount of the enantiomer pair, substantially free of other stereoisomers, to combat or to control pests (especially insects) and to a pesticidal composition comprising a pesticidally effective amount of the enantiomer pair, substantially free of other stereoisomers, and at least one carrier or surface active agent therefore. Suitable carriers and surface active agents are described in U.S. Pat. No. 4,042,710.

With respect to the spectrum of pesticidal activity, the enantiomer pair of this invention exhibits a selective or non-selective activity on such orders as Coleoptera, Lepidoptera (especially larvae), Diptera, Orthoptera, Hemiptera, Homoptera and Acarina. The compositions according to the present invention are very useful for controlling disease carrying insects such as mosquitoes, flies and cockroaches, grain insects such as rice weevil (*Sitophilus oryzae* Linne) and mites as well as agricultural noxious insects such as plant-hoppers, green rice leaf-hopper (*Nephotettix bipuntatus cinticeps* Uhler), diamond-back moths (*Plutella maculipennis* Curtis), imported cabbage worm (*Pieris rapae* Linne) rice stem borers (*Chilo suppressalis* Walker), corn earworm larvae (*Heliothis zea* Boddie), aphids tortrixes, leaf-miners and the like.

The enantiomer pair of the invention is used as a pesticide for harvested crops, horticultural application, forests, cultures in green house, and packaging materials for foodstuffs.

The compositions of the invention are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosages of toxicant of this invention at the locus to be protected—i.e., the applied dosage—is of the order of about 0.005 to about 0.5 kilograms per hectare, though under some circumstances the effective concentration will be as little as about 0.005 or as much as about 0.2, on the same basis.

ILLUSTRATIVE EMBODIMENTS

Embodiment I—Preparation

A 2 inch diameter chromatographic column packed with 360 g of silica gel (Grace Chemical Co., grade 62) was equilibrated with solvent, prepared by mixing 300 ml of diethyl ether with 4 l of redistilled hexane, by pumping the solvent thru the column from bottom to top for several hours until all gases were displaced from the column. 1.8 g of racemic R,S-α-cyano-3-phenoxybenzyl R,S-α-isopropyl-p-chlorophenyl-acetate in 15 ml of solvent was introduced into the column and eluted with 1200 ml of 1% ether in hexane followed by 2 l of 2% ether in hexane and thereafter hexane solvent with gradually increased ether content up to about 5%. After 2.2 l of liquid was eluted, 100 ml fractions of liquid were collected and analyzed by NMR for product ester content. Product ester was first seen in the 25th fraction. Fractions thereafter were combined as follows:

| Product | Fractions |
|---|---|
| A | 25–26 |
| B | 27 |
| C | 28–31 |
| D | 32–36 |
| E | 37–48 |
| F | 49–60 |

Products A and F were analyzed by infrared and nuclear magnetic proton analysis as enantiomer pairs: Product F, the later emerging pair, being the enantiomer pair consisting of S-α-cyano-3-phenoxybenzyl S-α-isopropyl-p-chlorophenylacetate and R-α-cyano-3-phenoxybenzyl R-α-isopropyl-p-chlorophenylacetate, substantially free of other stereoisomers; product A, earlier emerging pair, being the enantiomer pair consisting of S-α-cyano-3-phenoxybenzyl R-α-isopropyl-p-chlorophenylacetate and R-α-cyano-3-phenoxybenzyl S-α-isopropyl-p-chlorophenylacetate, substantially free of other stereoisomers. Products B thru E were various mixtures of the four possible stereoisomers.

Embodiment II—Pesticidal Activity

Activity of the enantiomer pair of this invention with respect to insect pests was determined by using standardized test methods to test the toxicity of the compounds as follows:

A. Houseflies (*Musca domestica* (Linne)) were tested by placing 50 4- to 5-day old houseflies into a spray cage and spraying with 0.6 ml of a solution in hexane of test compound. After spraying, the flies were anesthetized with $CO_2$ and transferred to a recovery cage containing a milk pad for food. The cages were held for 18–20 hours after which mortality counts were made. Both dead and moribund were counted. The tests were conducted employing several different dosage rates of each test compound.

b. Corn earworm larvae (*Heliothis zea* (Boddie)) were tested by spraying a broad bean plant with dilutions of hexane solutions of test compound into water containing an emulsifier. Immediately after spraying, 5 larvae were transferred to the plant and held for 44–46 hours, at which time the dead and moribund larvae were counted. The tests were conducted employing several different dosage rates for each test compound.

In each instance, the toxicity of the enantiomer pair of the invention was expressed in terms of the $LC_{50}$ dosage (in milligrams of test compound per 100 milliliters of solvent or liquid carrier in the solution or suspension of test compound used) required to kill 50 percent of the test insects. Tests were also conducted on the prior art racemic R,S-α-cyano-3-phenoxybenzyl R,S-α-isopropyl-p-chlorophenyl-acetate.

It can be seen from the results of these tests that the enantiomer pair of the invention exhibits toxicity against the various pests used in the test. Moreover, the enantiomer pair of the invention is up to about twice as active as the racemic R,S-α-cyano-3-phenoxybenzyl R,S-α-isopropyl-p-chlorophenylacetate.

PESTICIDAL ACTIVITY OF α-CYANO-3-PHENOXYBENZYL α-ISOPROPYL-p-CHLOROPHENYLACETATES EXPRESSED AS $LC_{50}$ DOSAGE

| | | House-fly | Corn earworm |
|---|---|---|---|
| R,S-α-cyano-3-phenoxybenzyl R,S-α-isopropyl-p-chlorophenylacetate | Racemic mixture of prior art | 0.00127 | 0.00053 |
| S-α-cyano-3-phenoxybenzyl S-α-isopropyl-p-chlorophenylacetate and R-α-cyano-3-phenoxybenzyl R-α-isopropyl-p-chlorophenylacetate | Enantiomer pair of the invention | 0.0007 | 0.00034 |

We claim:

1. An enantiomer pair consisting of S-α-cyano-3-phenoxybenzyl S-α-isopropyl-p-chlorophenylacetate and R-α-cyano-3-phenoxybenzyl R-α-isopropyl-p-chlorophenylacetate, said pair substantially free of other stereoisomers of α-cyano-3-phenoxybenzyl α-isopropyl-p-chlorophenylacetate.

2. An enantiomer pair according to claim 1 in a crystalline form.

3. A pesticidal composition which comprises, (a) as active ingredient, a pesticidally effective amount of an enantiomer pair consisting of S-α-cyano-3-phenoxybenzyl S-α-isopropyl-p-chlorophenylacetate and R-α-cyano-3-phenoxybenzyl R-α-isopropylp-chlorophenylacetate and (b) at least one surface-active agent or pesticide carrier, said composition substantially free of other stereoisomers of α-cyano-3-phenoxybenzyl α-isopropyl-p-chlorophenylacetate.

4. A method for controlling insects or acarids which comprises applying to said pest or their habitat an insecticidally or acaricidally effective amount of an enantiomer pair consisting of S-α-cyano-3-phenoxybenzyl S-α-isopropyl-p-chlorophenylacetate and R-α-cyano-3-phenoxybenzyl R-α-isopropyl-p-chlorophenylacetate, said pair substantially free of other stereoisomers of α-cyano-3-phenoxybenzyl α-isopropyl-p-chlorophenylacetate.

* * * * *